US012558169B2

(12) United States Patent
Schoepp et al.

(10) Patent No.: US 12,558,169 B2
(45) Date of Patent: Feb. 24, 2026

(54) TECHNIQUE FOR DETERMINING A MARKER ARRANGEMENT THAT DEFINES MARKER POSITIONS OF A TRACKER

(71) Applicant: Stryker European Operations Limited, Carrigtwohill (IE)

(72) Inventors: Hans Schoepp, Freiburg (DE); Fadi Ghanam, Schallstadt (DE)

(73) Assignee: Stryker European Operations Limited, Carrigtwohill (IE)

( * ) Notice: Subject to any disclaimer, the term of this patent is extended or adjusted under 35 U.S.C. 154(b) by 444 days.

(21) Appl. No.: 18/114,320

(22) Filed: Feb. 27, 2023

(65) Prior Publication Data

US 2023/0277251 A1 Sep. 7, 2023

(30) Foreign Application Priority Data

Mar. 1, 2022 (EP) ..................................... 22159345

(51) Int. Cl.
 *A61B 5/00* (2006.01)
 *A61B 34/20* (2016.01)
 *G06T 7/73* (2017.01)

(52) U.S. Cl.
 CPC ................ *A61B 34/20* (2016.02); *G06T 7/73* (2017.01); *A61B 2034/2068* (2016.02); *G06T 2207/10081* (2013.01); *G06T 2207/10088* (2013.01); *G06T 2207/30204* (2013.01)

(58) Field of Classification Search
 CPC ......................... A61B 34/20; A61B 2034/2068
 See application file for complete search history.

(56) References Cited

U.S. PATENT DOCUMENTS

| 7,876,942 B2 | 1/2011 | Gilboa |
| 9,622,824 B2 | 4/2017 | Goldbach |
| 2017/0348061 A1 | 12/2017 | Joshi et al. |

(Continued)

FOREIGN PATENT DOCUMENTS

| CN | 113925609 A | 1/2022 |
| EP | 1872735 B1 | 5/2016 |

(Continued)

OTHER PUBLICATIONS

English language abstract and machine-assisted English translation for CN 113 925 609 A extracted from espacenet.com database on Feb. 27, 2023, 9 pages.

(Continued)

*Primary Examiner* — Joel F Brutus
(74) *Attorney, Agent, or Firm* — Howard & Howard Attorneys PLLC

(57) ABSTRACT

A method, a computer program product, a device, and a surgical navigation system for determining a marker arrangement that defines positions of markers of a tracker are provided. The markers are detectable by a first imaging modality and a second imaging modality that is different from the first imaging modality. The method comprises receiving first image data of the markers that were captured using the first imaging modality and receiving second image data of the markers that were captured using the second imaging modality. The method further comprises determining the marker arrangement based on the first and second image data.

17 Claims, 11 Drawing Sheets

100

102 Receive first image data of markers that were captured using a first imaging modality 104 Receive second image data of the markers that were captured using a second imaging modality 106 Determine a marker arrangement based on the first and second image data

(56) References Cited

U.S. PATENT DOCUMENTS

2017/0360517 A1    12/2017  Crawford et al.
2018/0028133 A1     2/2018  Jones et al.
2021/0236208 A1     8/2021  Drexl et al.
2022/0008141 A1*    1/2022  Chopra ................. A61B 6/461

FOREIGN PATENT DOCUMENTS

EP          3556312  A1    10/2019
WO       2013192598  A1    12/2013

OTHER PUBLICATIONS

English language abstract for EP 1 872 735 B1 extracted from espacenet.com database on Feb. 27, 2023, 2 pages.

* cited by examiner

102 — Receive first image data of markers that were captured using a first imaging modality 104 — Receive second image data of the markers that were captured using a second imaging modality 106 — Determine a marker arrangement based on the first and second image data

100

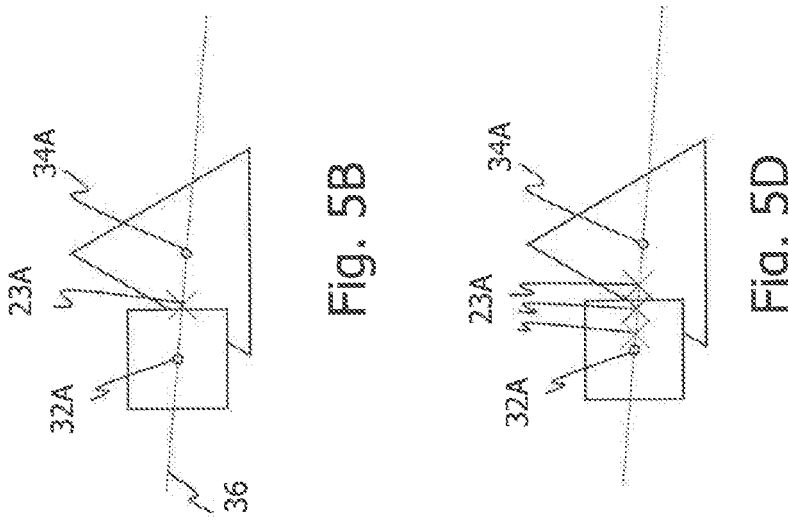
Fig. 5A
Fig. 5B
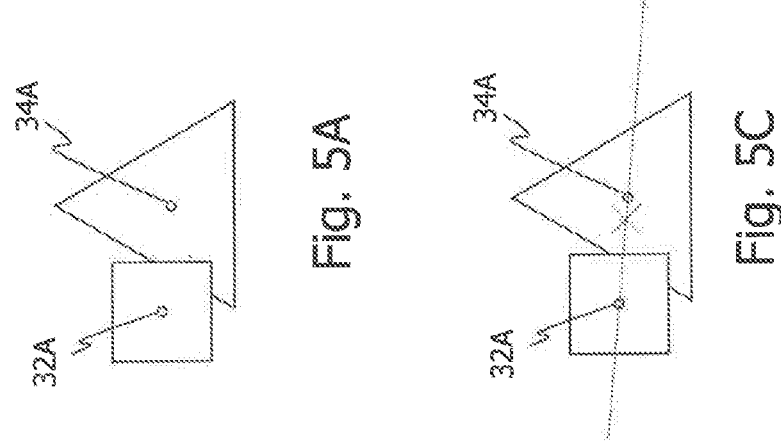
Fig. 5C
Fig. 5D

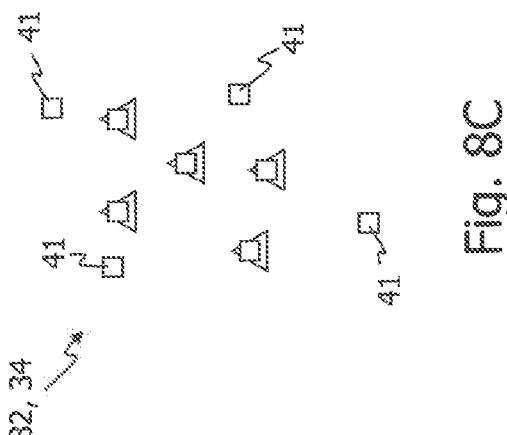
Fig. 8C
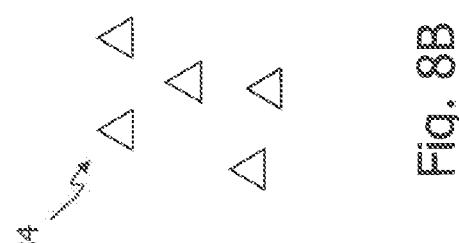
Fig. 8B
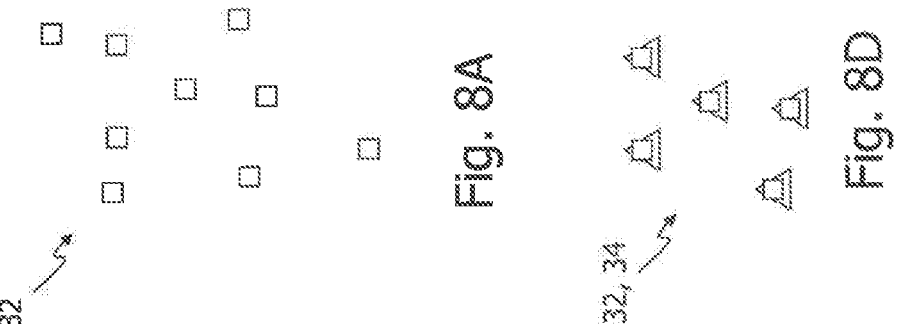
Fig. 8A
Fig. 8D

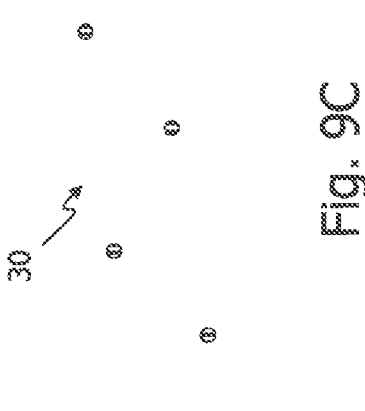
Fig. 9C
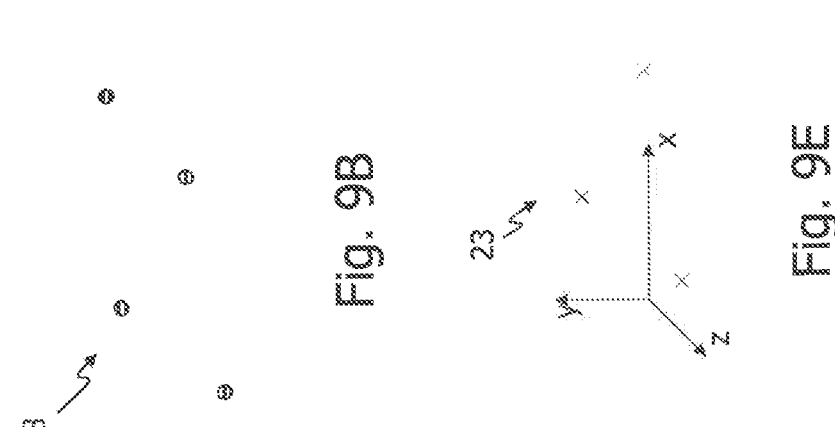
Fig. 9B
Fig. 9E
Fig. 9A
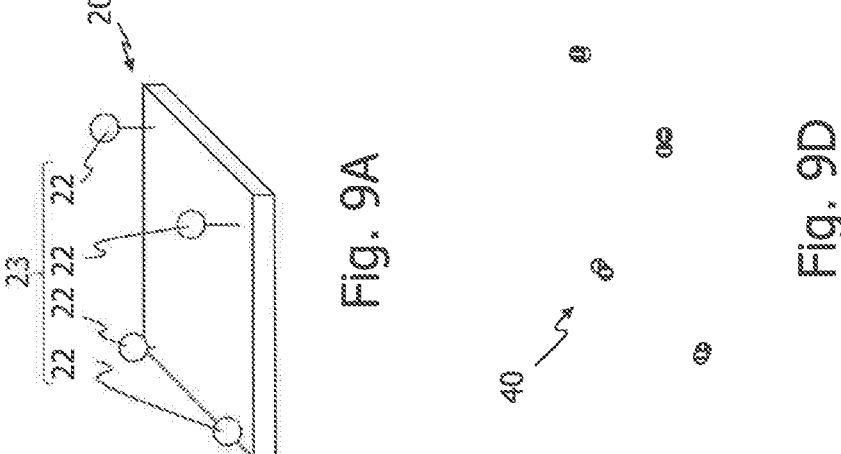
Fig. 9D

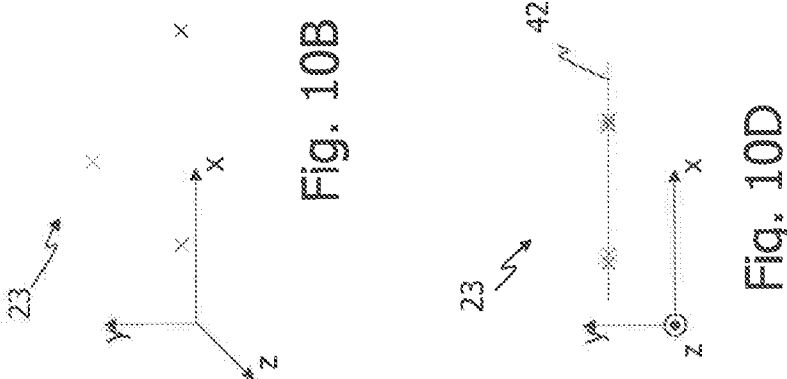
Fig. 10B
Fig. 10D
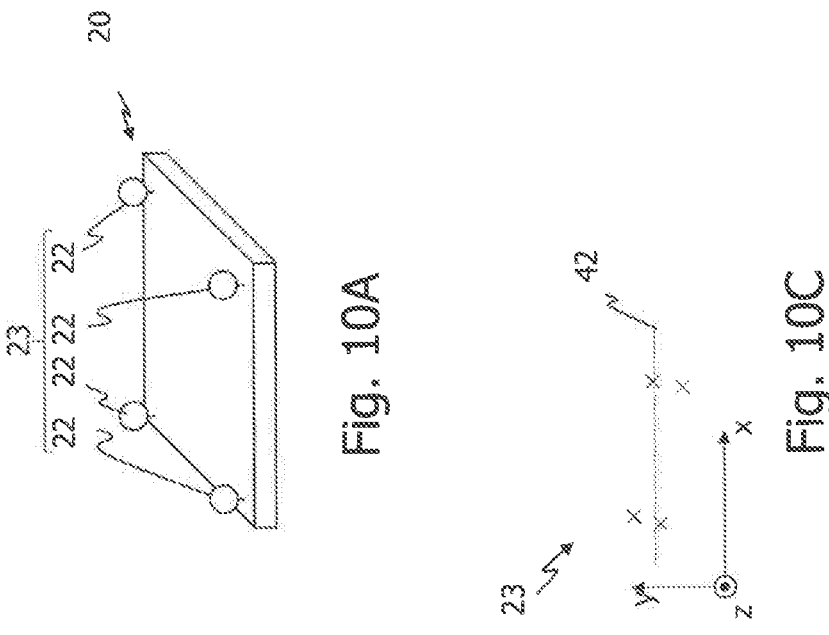
Fig. 10A
Fig. 10C

TECHNIQUE FOR DETERMINING A MARKER ARRANGEMENT THAT DEFINES MARKER POSITIONS OF A TRACKER

PRIORITY CLAIM

This application claims priority under 35 U.S.C. § 119 to European Patent Application No. 22159345.2, filed Mar. 1, 2022, the entire contents of which are hereby incorporated by reference.

TECHNICAL FIELD

The present disclosure generally relates to tracking in, for example, a surgical navigation context. In more detail, a technique for determining a marker arrangement that defines positions of markers of a tracker is presented. The technique may be implemented as a method, a computer program product, a device, or a surgical tracking system.

BACKGROUND

Surgical tracking systems are configured to track surgical objects, such as a surgical instrument or a patient in an operating room. A commonly used tracking technique involves a tracker with optical markers as well as a camera capable of detecting light emitted or reflected by the markers. Based on the detected light, the tracking system determines information on one or both of a position and an orientation of the tracker and, thus, of the surgical object to be tracked.

In order to determine the position or orientation of the tracked surgical object using image data generated by the camera, an arrangement of the markers needs to be known to the tracking system. For example, the tracking system may require knowledge about the marker arrangement for accurately locating the tracker or for differentiating a particular tracker from other trackers. The marker arrangement may, for example, be evaluated by the tracking system in the form of positional coordinates of the markers in a given coordinate system.

However, there may be no, or no sufficiently accurate, knowledge about the marker arrangement in certain scenarios. Such scenarios include the case of a tracker that has intentionally or unintentionally been deformed prior to or during a surgical intervention, a customizable tracker that may have been configured in a patient-specific manner, or a disposable tracker that has been manufactured with larger manufacturing tolerances.

SUMMARY

There is a need for a technique that permits a proper determination of a marker arrangement that defines positions of the markers of a tracker.

According to one aspect, a method for determining a marker arrangement that defines positions of markers of a tracker is provided. The markers are detectable by a first imaging modality and a second imaging modality that is different from the first imaging modality. The method comprises receiving first image data of the markers that were captured using the first imaging modality and receiving second image data of the markers that were captured using the second imaging modality. The method further comprises determining the marker arrangement based on the first and second image data.

The marker arrangement may define positions of the markers relative to each other. Additionally, or in the alternative, the marker arrangement may define positions of the markers in a common coordinate system. As an example, determining the marker arrangement may comprise determining coordinates of the positions of two or more, or all, of the markers in a coordinate system. As a further example, determining the marker arrangement may comprise determining relative positions of the markers (e.g., in the form of relative distances and/or orientations).

At least one of the first and second image data may be representative of at least one of an image, a plurality of images, a video, a point cloud, and a polygon mesh. At least one of the first and second image data may comprise information related to at least one of a viewing angle, viewing distance, and time of capturing the respective image data.

At least one of the markers may have a first marker portion detectable by the first imaging modality and a second marker portion spaced apart from the first marker portion and detectable by the second imaging modality. The first marker portion may be arranged in a pre-determined geometrical relationship relative to the second marker portion. The marker arrangement may be further determined based on the pre-determined geometrical relationship.

The first marker portion may include a material configured to reflect or emit electromagnetic radiation that can be sensed by a camera (e.g., at least one of infrared light, visible light, and ultraviolet light). The second marker portion may comprise material detectable in a computed tomography (CT) scan or magnetic resonance imaging (MRI) scanner.

At least one of the markers may have a third marker portion detectable by both the first imaging modality and by the second imaging modality. At least one of the markers may have only the third marker portion or only the first and second marker portions. As an example, the third marker portion may include one or more materials that can be detected by both the first and the second imaging modality. The third marker portion may have a spatial extension that does not significantly (e.g., by more than 50%) exceed a spatial resolution of one or both of the first imaging modality and the second imaging modality.

One of the first and second imaging modality may comprise one of a CT scanner and an MRI scanner. The other one of the first and second imaging modality may comprise at least one camera (e.g., a stereo camera). The camera may be configured to detect electromagnetic radiation (e.g., at least one of infrared light, visible light, and ultraviolet light).

The markers of the tracker may be arranged in a common plane. Determining the marker arrangement may include virtually arranging the positions of the markers in a virtual plane that is determined based on at least one of the first and second image data. The virtual plane may be determined based on a preliminary marker arrangement and before the actual, or final, marker arrangement is determined taking into account the virtual plane. The virtual plane may be determined from at least one of the first and second image data.

The method may comprise registering at least one of the first and second image data, or third image data, with the tracker using the determined marker arrangement. The method may comprise registering a CT or MRI scan from one of the first and the second imaging modality (e.g., one of the first and second image data or the third image data that have been acquired after the first and second image data) with the tracker using the determined marker arrangement. The method may comprise tracking (and, optionally, visualizing) at least one of a position and an orientation of a surgical object carrying with tracker relative to the registered image data.

The tracker may have a deformable substrate supporting the markers, wherein the markers are arranged in a predetermined (e.g., planar) arrangement for an undeformed shape of the substrate. Determining the marker arrangement for a deformed shape of the substrate may be further based on the pre-determined arrangement. The deformable substrate may be at least one of bendable, stretchable, and compressible. The substrate may comprise a face or spine mask configured to adapt to the surface of a patient's face or back.

The method may comprise determining, based on the first image data, a first arrangement that defines first positions of the markers and determining, based on the second image data, a second arrangement that defines second positions of the markers. The marker arrangement may be determined based on a combination of the first and second arrangements.

The marker arrangement may be determined based on averaged positions of the markers between the first and second arrangement. The marker arrangement may be determined based on weighted averaged positions of the markers between the first and second arrangement. For example, the positions of a particular marker in the first arrangement and in the second arrangement may be processed to calculate an (optionally weighted) averaged position.

In some cases, the average is weighted towards the first or second arrangement. The average may be weighted more towards the imaging modality with the larger spatial resolution (e.g., the larger spatial resolution of the markers). Alternatively, or in addition, the average may be weighted based on one or more of (i) a temporal sequence in which the first and second image date have been taken and (ii) at least one of a viewing angle and a viewing distance of at least one of the first and second imaging modality. The average may be weighted more towards the more recently captured image data. The first image modality (or alternatively the second image modality) may comprise a camera, and the average may be weighted more towards the first imaging modality with decreasing viewing distance of the camera when capturing the first image data. The average may be weighted more towards the more recently captured image data the larger a time difference between capturing the first and second image data is.

The method may comprise determining an invalid position of a particular marker in at least one of the first or second arrangement. The method may comprise disregarding the invalid position of the particular marker in the at least one of the first or second arrangement when determining the position of the particular marker in the marker arrangement. A position of the particular marker may be determined as invalid if the position cannot be determined from the respective image data. The position of the particular marker may be determined as invalid if a distance of the position relative to an expected position and/or positions of one or more other markers (e.g., in the same marker arrangement or in the other marker arrangement) exceeds a threshold.

The method may comprise generating an error signal when a quality criterion between positions of a marker in the first arrangement and the second arrangement fulfils an error condition. The quality criterion may comprise a distance between positions of a marker of the first and second marker arrangement. The quality criterion may alternatively or additionally comprise an existence of a determinable position of the first and second marker arrangements.

The method may further comprise attempting to match the first positions of the first arrangement with the second positions of the second arrangement. Any matching algorithm can be used in this regard. The method may further comprise disregarding at least one of the first positions that lacks a matching second position. Additionally, or in the alternative, the method may comprise disregarding at least one of the second positions that lacks a matching first position. Determining the marker arrangement based on the first and second image data may then be performed excluding (e.g., "filtering out") the one or more disregarded positions.

Matching (e.g., aligning) the first and second positions may comprise using a point-set algorithm, for example an algorithm for minimizing a difference between the first and second positions, such as the Iterative Closest Point (ICP) algorithm. A so-called "spare" first or second position may be considered to lack a matching second or first position to be aligned with in at least one of the following cases: (i) the "spare" first or second position lacks a matching second or first position within a threshold distance, and (ii) the "spare" first or second position does not meet an alignment criterion of the used point-set algorithm.

The method may further comprise determining combined image data based on the first and second image data. The marker arrangement may be determined based on the combined image data. Combining the image data may comprise tracking an imaging device of one of the first and second imaging modalities using the other one of the first and second imaging modality. Combining the image data may comprise identifying markers in the first and second image data and aligning the identified markers of the first and second image data.

According to a second aspect, a computer program product is provided. The computer program product comprises instructions that, when executed on at least one processor, cause the at least one processor to carry out any of the methods described herein. The computer program product may be stored on a non-volatile storage medium such as a hard drive, a compact disc, a flash drive, a cloud computing device or a download server.

According to a third aspect, a device for determining a marker arrangement that defines positions of markers of a tracker is provided. The markers are detectable by a first imaging modality and a second imaging modality that is different from the first imaging modality. The device is configured to receive first image data of the markers that were captured using the first imaging modality and receive second image data of the markers that were captured using the second imaging modality. The device is further configured to determine the marker arrangement based on the first and second image data.

The device may be configured to perform any method aspect and method step as described herein.

According to a fourth aspect, a surgical tracking system is provided that comprises the device described herein and the tracker, wherein the tracker is attached or comprises an interface configured to be attached to a surgical object (e.g., a patient or a surgical instrument). The interface may comprise at least one of an adhesive, a clamp, a screw, and a magnet.

BRIEF DESCRIPTION OF THE DRAWINGS

Further details, advantages and aspects of the present disclosure will become apparent from the following embodiments taken in conjunction with the drawings, wherein:

FIG. 5A shows for one of the markers a first position of the first marker arrangement and a second position of the second marker arrangement;

FIG. 5B shows a marker position determined as an average position between the first position and the second position;

FIG. 5C shows a marker position determined as a weighted averaged position between the first position and the second position FIG. 5D shows different marker positions resulting from different weight criteria;

FIG. 8A shows an example of a first arrangement of markers and non-markers determined from a first image data;

FIG. 8B shows an example of a second arrangement without non-markers determined from a second image data;

FIG. 8C shows the first arrangement depicted in FIG. 8A in alignment with the second arrangement depicted in FIG. 8B;

FIG. 8D shows the first and second positions depicted in FIG. 8C, wherein spare first positions are disregarded;

FIG. 9A shows an example of a tracker with four markers, which are arranged in a pre-defined marker arrangement, similar to FIG. 4A;

FIG. 9B shows first image data captured of the markers shown in FIG. 9A;

FIG. 9C shows second image data captured of the markers shown in FIG. 9A;

FIG. 9D shows a combined image data that comprises the first image data and the second image data;

FIG. 9E shows a marker arrangement determined from the combined image data depicted in FIG. 9D;

FIG. 10A shows an example of a tracker with four markers, wherein the markers are arranged in a common plane;

FIG. 10B shows a marker arrangement of the tracker shown in FIG. 10A determined by any of the methods described herein;

FIG. 10C shows a side view of the marker arrangement of FIG. 10B;

FIG. 10D shows the determined marker arrangement, wherein the positions of the marker arrangement are located on a virtual plane;

DETAILED DESCRIPTION

Figure 1:
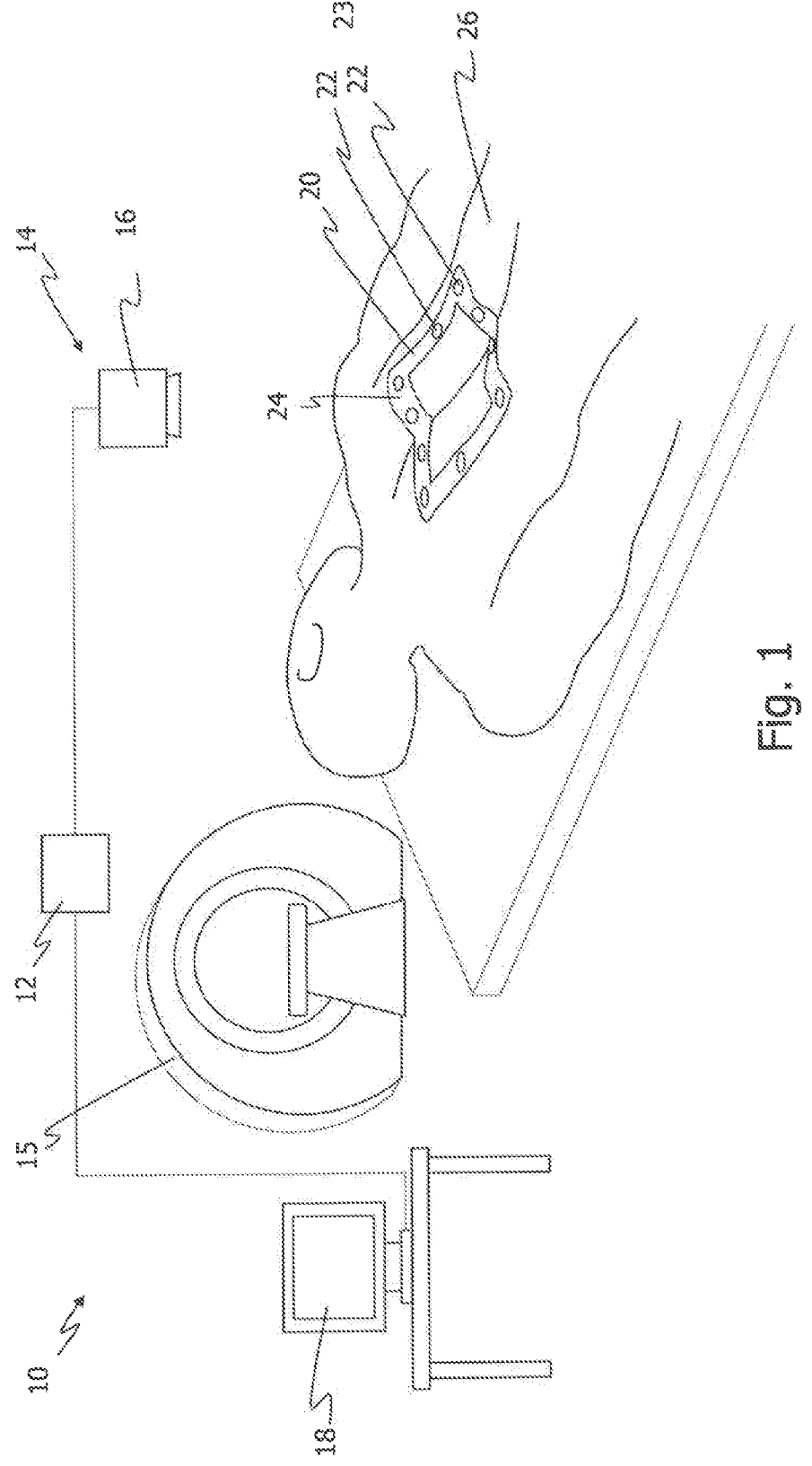
FIG. 1 shows a surgical tracking and navigation system comprising a device according to the present disclosure.

FIG. 1 shows a surgical tracking and navigation system 10 comprising a marker arrangement determining device 12 according to the present disclosure. The device 12 is implemented as a local computer system in an operating room. Alternatively, the device 12 may at least partially be provided by a remote server or cloud computing resources.

The surgical tracking and navigation system 10 further comprises a tracking system 14 with a camera 16. Alternatively, the tracking system 14 may comprise multiple cameras 16, such as in form of separately provided cameras or a stereo camera. The tracking system 14 may further comprise processing components (not shown). Such processing components may be shared with the marker arrangement determining device 12 (e.g., in the form of a local computer system). In some variants, the marker arrangement determining device 12 is integrated into the tracking system 14 (e.g., in the form of an integrated software product).

At least one of the tracking system 14 and the marker arrangement determining device 12 may comprise or be communicatively coupled with an output device 18. The exemplary output device 18 depicted in FIG. 1 comprises a display (e.g., a computer monitor or tablet). Alternatively or additionally, the output device may comprise at least one of a speaker, virtual reality glasses, glasses with a head-up-display, and a haptic feedback device.

The surgical tracking and navigation system 10 further comprises a tracker 20 as a component of the tracking system 14. The tracker 20 is generally configured to be attached to a surgical object, such as patient 26. In the present realization, the tracker 20 supports typically multiple markers 22. Each marker 22 may be an electromagnetically passive or active element. For example, at least one of the markers 22 may be a passive element configured to reflect electromagnetic radiation, such as a flat reflective surface, a sphere, or a reflective printed surface. Additionally or alternative, at least one of the markers 22 may be an active element capable of emitting electromagnetic radiation such as a light emitting diode (LED) or an incandescent light bulb (any of which may be coupled to an optical fibre). The camera system 14 is capable of detecting the electromagnetic radiation reflected or emitted by the markers 22.

The tracker 20 is arranged on a surface of the patient 26 (e.g., the patient's back as depicted in FIG. 1) or any surgical instrument or other surgical object. To this end, the tracker 20 comprises an interface configured to be attached to the surgical object. The interface may comprise at least one of an adhesive, a clamp, a screw, and a magnet. The tracker 20 shown in FIG. 1 comprises an interface in form of an adhesive that allows the tracker to be adhesively attached to the skin of the patient's back. However, the tracker 20 may be attached to any other surface of the patient 26, such as the face or an extremity. Moreover, the tracker 20 may be arranged on or attached to any other surgical object, such as a surgical instrument, a surgical frame, a tracking system component, or an imaging device. The tracker 20 depicted in FIG. 1 is a single device. Alternatively, the tracker 20 may comprise separate tracking portions that can be individually attached to the surgical object, wherein each tracking part supports at least one marker. These separate tracking portions will then collectively form the tracker 20.

The markers 22 are arranged according to a marker arrangement 23 that defines (e.g., relative) positions of the markers 22. The tracker 20 depicted in FIG. 1 has a flexible substrate 24 that supports the markers 22. The substrate 24 may be at least one of compressible and stretchable. The substrate 24 thus accommodates to the skin surface of the patient 26 and, as such, assumes a deformed state. As a result, the marker arrangement 23 in the deformed state of the substrate 24 may be unknown a priori to the tracking system 14 before the surgical procedure starts or during the surgical procedure. Determining the marker arrangement 23 in the deformed state is necessary for tracking the tracker 20 by the tracking system 14 (e.g., for reliably recognizing the marker arrangement 23 in tracking image data taken by the camera 16) and for surgical navigation.

A flexible substrate 24 as depicted in FIG. 1 is one of many possible reasons why the marker arrangement 23 may not be known a priori. In other cases, the tracker 20 may have a rigid substrate, but the substrate may be bent (e.g., intentionally by a user or unintentionally by wear or impacts). In still further cases, the tracker 20 may have been manufactured with large tolerances (e.g., using an additive manufacturing technique such as 3D printing). In the case of a customizable tracker 20 with a plurality of movable, attachable or detachable tracking portions, the marker arrangement 23 may be arranged by the surgeon in a customized manner prior to the surgical procedure.

The marker arrangement 23 may be determined solely from first image data captured using a first imaging modality such as the camera system 14. However, determining the marker arrangement 23 based on the first image data only may not be sufficiently accurate (e.g., in terms of insufficient spatial resolution or in terms of obstruction) for surgical navigation purposes. As such, a more accurate technique for determining the marker arrangement 23 by marker arrangement determining device 12 is proposed.

Image data may be captured from the tracker 20 using two different imaging modalities. For example, in the case where a CT scan of the patient 26 is taken, second image data of the patient 26 with the tracker 20 is captured using a CT scanner 15 as second imaging modality, whereas the camera system 14 as the first imaging modality captures first image data of the tracker 20. The markers 22 of the tracker 20 can be identified by the marker arrangement determining device 12 in the first and second image data, which, for example, allows registering the second image data with the tracker 20 (and, thus, the patient 26) in a coordinate system of the tracking system 14.

In order to be able to identify the markers 22 in both imaging modalities, the markers 22 are configured to be detectable by both imaging modalities. Various possibilities exist in this regard.

Figures 2A, 2B, 2C, 2D, 2E, 2F:
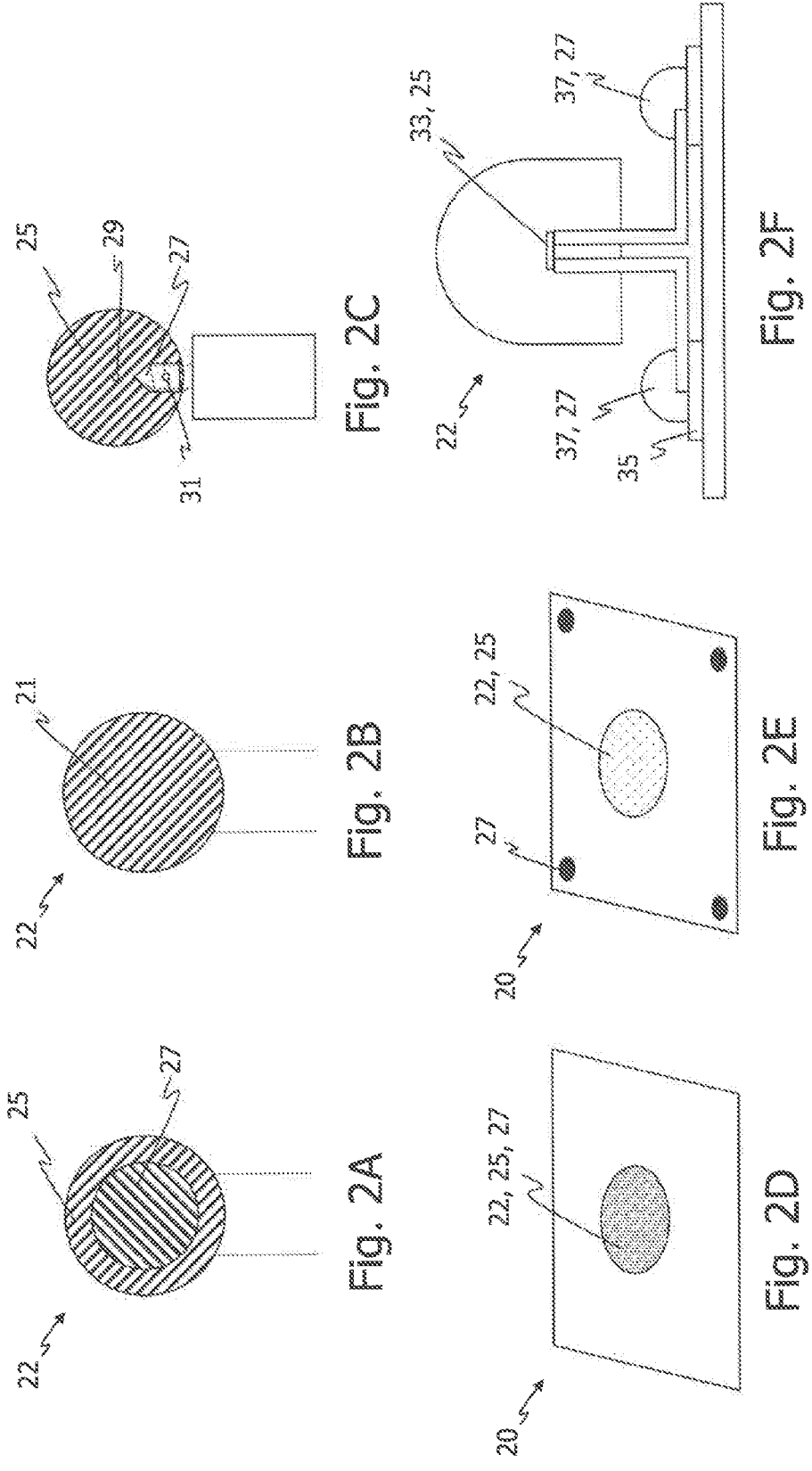
FIG. 2A shows a cross-section of a first example of a passive marker with a first marker portion and a second marker portion.
FIG. 2B shows a cross-section of a second example of a passive marker comprising a third marker portion.
FIG. 2C shows a cross-section of a third example of a passive marker with a first marker portion spatially offset relative to a second marker portion.
FIG. 2D shows a perspective view of a first example of a printed tracker.
FIG. 2E shows a perspective view of a second example of a printed tracker.
FIG. 2F shows an example of an active marker with an LED electrically connected to a circuit with solder joints.

FIG. 2A shows a cross-section of a first example of a passive marker 22 with a first marker portion 25 detectable by the first imaging modality (here: the camera 16) and a second marker portion 27 detectable by the second imaging modality (here: the CT scanner 15). In the example shown in FIG. 2A, the first marker portion 25 is a shell and the second marker portion 27 is a sphere that is concentrically arranged relative to the shell of the first marker portion 25. Therefore, positions (e.g., in terms of a respective centre) determined for the marker 22 in the first image data and the second image data are at least essentially identical.

FIG. 2B shows a cross-section of a second example of a passive marker 22 comprising a third marker portion 21 that comprises material detectable by both imaging modalities (here: detectable by the camera 16 and the CT scanner 15). Therefore, positions determined for the marker 22 in the first image data and the second image data are at least essentially identical.

FIG. 2C shows a cross-section of a third example of a passive marker 22 with a first marker portion 25 spatially offset relative to a second marker portion 27. In the example shown in FIG. 2C, the first marker portion 27 is a sphere that is screwed onto a screw-shaped second marker portion 27. In contrast to the scenario of FIG. 2A, a centre position 29 of the first marker portion 25 does not coincide with a centre position 31 of the second marker portion 27. However, a geometrical relationship (e.g., in terms of a vector or a spatial translation between the position 29 and the position 31) may be pre-determined, which means that it is known a priori prior to the surgical procedure. As a result, the position of the second marker portion 27 can be determined using the position of the first marker portion 25 and the pre-determined geometrical relationship (and vice versa).

FIG. 2D shows a perspective view of a first example of a printed tracker 20. The tracker 20 has a printed marker 22 detectable by the first imaging modality and second imaging modality. For example, the marker 22 may be printed with ink that includes infrared light-reflecting pigments detectable by the camera system 14 and metal particles visible in a CT scan.

FIG. 2E shows a perspective view of a second example of a printed tracker 20. The tracker 20 has a marker 22 with a first marker portion 25 that is detectable by the first imaging modality and second marker portions 27 detectable by the second imaging system. The second marker portions 27 may be printed or comprise attachment elements (e.g., a screw, nail or staple).

FIG. 2F shows an example of an active marker 22 with an LED 33 electrically connected to a circuit 35 with at least one (here: two) solder joints 37. The marker 22 comprises a first marker portion 25 in form of the LED 33, as the LED is detectable by the first imaging modality in form of the camera 16. The marker 22 furthermore comprises two second marker portions 27 in form of the solder joints 37, which are detectable by the second imaging modality in form of the CT scanner 15. A geometrical relationship between the first marker portion 25 and the two second marker portions 27 may be pre-determined.

As can be seen in the examples shown in FIGS. 2E and 2F, each marker 22 does not necessarily comprise exactly one marker portion 25, 27. Instead, a marker may comprise more than one first marker portion 25 and/or more than one second marker portion 27.

Figure 3:
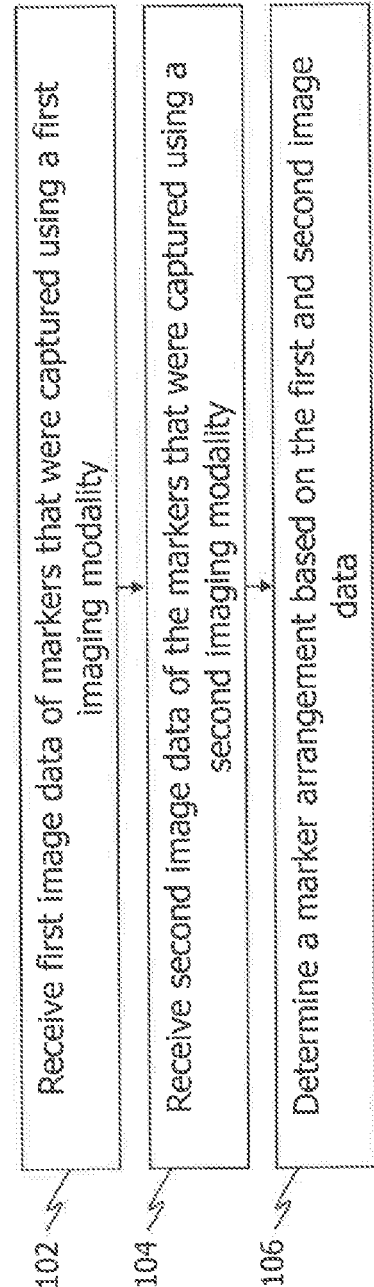
FIG. 3 shows a flow diagram of a method for determining a marker arrangement that defines positions of markers of a tracker.

FIG. 3 shows a flow diagram 100 of a method for determining a marker arrangement 23 that defines positions of markers 22 of a tracker 20. The marker arrangement determining device 12 of FIG. 1 is configured to perform any of the method steps described herein. To this end, the device 12 may comprise at least one processor, wherein a computer program product executed by the at least one processor causes the at least one processor to carry out any of the method steps described herein.

The method comprises in step 102 receiving first image data of the markers 22 that were captured using the first imaging modality. To this end, the markers 22 are detectable by the first imaging modality. As mentioned above, the first imaging modality can be the camera 16. Therefore, the camera 16 can function both for tracking the tracker 20 with the markers 22 as well as for imaging the marker arrangement 23 prior to the actual tracking during a surgical procedure. Alternatively, different cameras or camera systems may be used to capture the first image data for calibration purposes (i.e., accurately determining the marker arrangement 23) and to track the tracker 20. The camera or camera system to capture the first image data may have a higher spatial resolution, but does not have to meet additional requirements for tracking (such as a high frame rate).

The first image data may be representative of one or more images or one or more videos of the markers 22. At least one of the images or videos may be captured from different viewing angles. For example, the first image data may be captured by a stereo camera or by a single camera that is moved relative the tracker 20.

The method comprises in step 104 receiving second image data of the markers that were captured using the second imaging modality. The second imaging modality is different from the first imaging modality. The markers 22 are also detectable by the second imaging modality. In the example of FIG. 1, the first imaging modality comprises a CT scanner 15. The second imaging modality may alternatively comprise a magnetic resonance imaging (MRI) device. Steps 102 and 104 may be performed in any order and also in parallel.

The method further comprises in step 106 determining the marker arrangement based on the first and second image data. In the process of determining the marker arrangement 23 based on the first and second image data, positions of the markers 22 in at least one of the first image data, the second image data or combined image data derived from the first and second image data are determined. The position (e.g. coordinates) of a particular marker 22 may be determined in any of the image data using image processing techniques that may be based on an image point (such as a pixel) with a highest intensity, an image point with a large contrast or large intensity change, or at a geometric centre of a plurality of such image points.

Determining the marker positions may include locating the marker positions spatially offset relative to the above determined image points. The spatial offset may be determined based on the geometrical relationship between the first and second marker portions 25, 27 (see FIGS. 2C, 2E and 2F). In case one of the first and second modalities is used for subsequent tracking, the position determined in the image data using the other imaging modality may be spatially offset towards the marker portion of the tracking imaging modality.

For example, first image data of the marker 22 shown in FIG. 2F may be captured by the camera 16 and second image data may be captured by the CT scanner 15. Image points of the second marker portions 27 (i.e., the solder joints 37) may be located in the second image data and subsequently spatially offset using the known (i.e., pre-determined) geometrical relationship to align with the position of the first marker portions 25 (e.g., the LED 33). As a result, positions of the first marker portion 25, i.e., the LED 33, can be located in both, the first and second image data. Using the positions of the first marker portions 25 for determining the marker arrangement may be more representative of the position of the LEDs 33 and therefore more accurate for subsequent tracking.

Similarly, the positions of the first marker portions 25 (e.g., the LED 33) determined from image points in the first image data (captured by the camera 16) may be shifted using the geometrical relationship to align with the image points of the second marker portions 27 (i.e., the solder joints 37). As a result, positions of the second marker portion 27 can be located in both, the first and second image data. Using the positions of the second marker portions 27 for determining the marker arrangement may be more representative of the position of the solder joints 37 and therefore more accurate for registering the second image data with the tracker 20.

Determining the marker arrangement 23 may be performed according to a first or second approach as will now be described in greater detail. Of course, other approaches could be used as well. According to the first approach, the method further comprises determining, based on the first image data, a first arrangement that defines first positions of the markers 22 and determining, based on the second image data, a second arrangement that defines second positions of the markers 22. In such a case, the marker arrangement 23 is determined based on a combination of the first and second arrangements. This approach will now be explained with reference to FIGS. 4A to 4E.

Figures 4A, 4B, 4C, 4D, 4E, 4F:
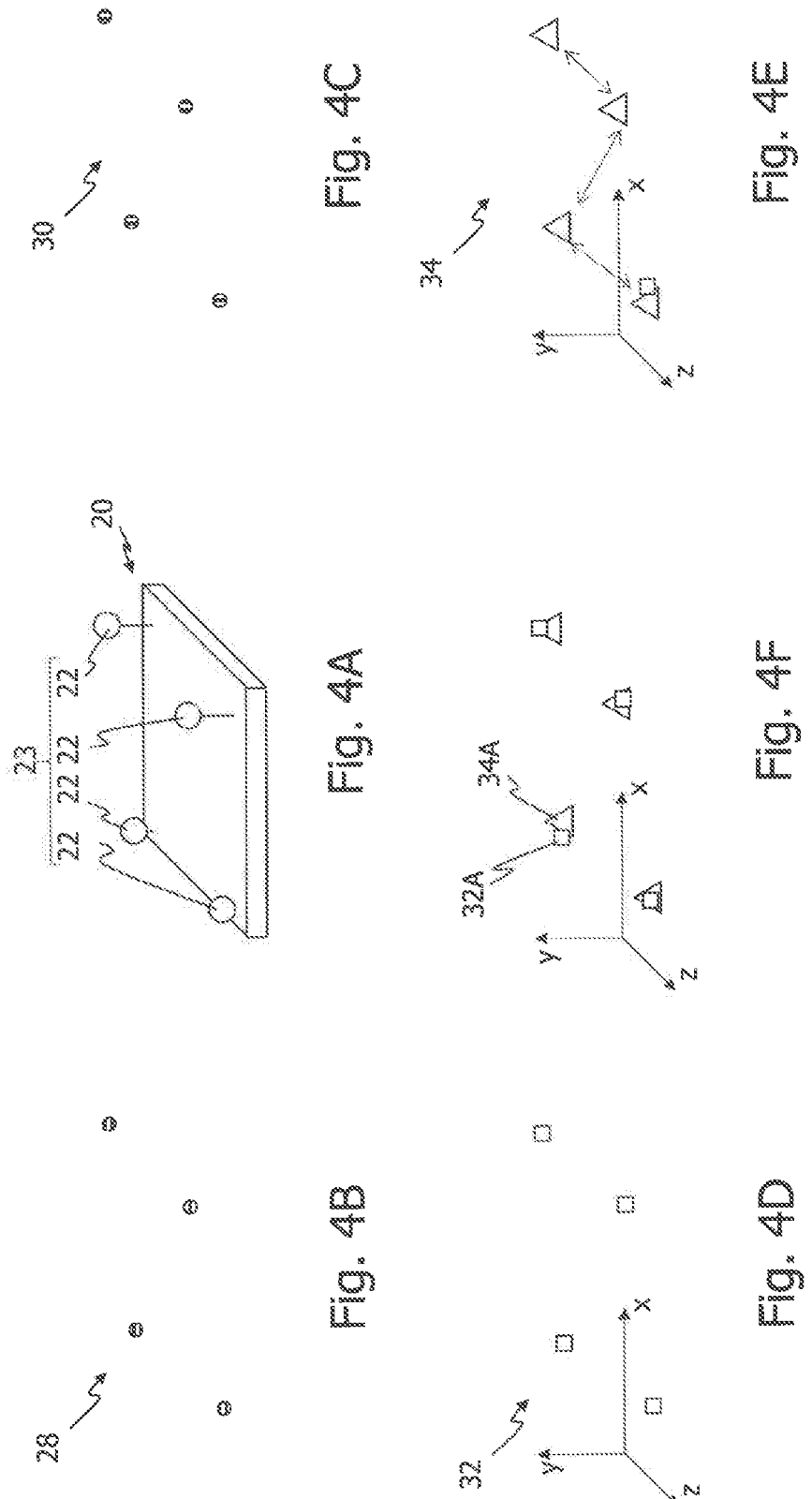
FIG. 4A shows an example of a tracker with four markers, which are arranged in a pre-defined marker arrangement.
FIG. 4B shows a representation of first image data of the tracker markers.
FIG. 4C shows an example of second image data of the tracker markers.
FIG. 4D shows a first marker arrangement determined based on the first image data.
FIG. 4E shows a second marker arrangement determined based on the second image data.
FIG. 4F shows a combination of the first marker arrangement and the second marker arrangement.

FIG. 4A shows an example of a tracker 20 with four markers 22, which are arranged in a given marker arrangement 23 to be used during a surgical procedure. The tracker 20 may have any other number of markers 22, such as two, three, five, or more markers 22. The markers 22 in FIG. 4A are purposefully arranged at random positions in order to better represent an unknown marker arrangement 23 (e.g., resulting from a deformed marker substrate 24, see FIG. 1).

FIG. 4B shows a representation of first image data 28. The first image data 28 may be derived from one or more images of the markers 22 (e.g., as captured by the camera 16). The first image data 28 may comprise data indicating captured intensity or contrasts of the markers 22, as illustrated in FIG. 4B. As such, the markers 22 as represented in the first image data 28 may have a spatial extension.

FIG. 4C shows a representation of second image data 30 (e.g., as taken by the CT scanner 15). The second image data 30 may be defined similarly as the first image data 28. The second image data 30 may be derived from at least one of X-ray projections through the markers 22, cross sectional images slices of the markers 22, and a volume rendering of the markers 22.

FIG. 4D shows a first marker arrangement 32 determined based on the first image data 28. The first marker arrangement 32 (or any marker arrangement described herein) may be defined in a manner that directly or indirectly defines positions of the markers 22 relative to each other. For example, the first marker arrangement 32 may define marker positions in a common coordinate system. Alternatively or additionally, the first marker arrangement 32 may define positions of markers 22 relative to other markers 22. In the example depicted in FIG. 4D, the first marker arrangement 32 defines positions of markers 22 in a common coordinate system. If the markers 22 as represented in the first image data 28 have a spatial extension, image processing techniques may be applied to derive dedicated marker coordinates, as explained above.

FIG. 4E shows a second marker arrangement 34 determined based on the second image data 30. The second marker arrangement 34 may be defined in a similar or different manner than the first marker arrangement 32. In the example depicted in FIG. 4E, the second marker arrangement 34 defines positions of markers 22 relative to other markers 22.

FIG. 4F shows a combination of the first marker arrangement 32 (in form of square icons) and the second marker arrangement 34 (in form of triangles) in a common coordinate system. While the positions of each marker 22 are similar in the first and second marker arrangement 32, 34, the positions are not identical, as they are each determined from different image data (and possibly at different spatial resolution, different angles, etc.). The marker arrangement 23 of interest can be determined in step 106 of FIG. 3 based on the first and second marker arrangements 32, 34 in different ways, as will be described below.

FIG. 5A shows for an exemplary one of the markers 22 a first position 32A of, or in, the first marker arrangement 32 and a second position 34A of, or in, the second marker arrangement 34B. While the square shape and the triangle shape allows differentiating between the first and second marker arrangements 32, 34, the actual position (e.g., the actual coordinates) is indicated by a circle centrally in each of the two shapes.

FIG. 5B shows a position 23A of a first marker of the marker arrangement 23 determined in step 106 of FIG. 3 as an average position between the first position 32A and the second position 34A. The determined (here: averaged) position 23A of the first marker may be determined by defining a connecting line 36 between the first and second positions 32A, 34A and locating the determined position on the connecting line 36 at an equal distance to the first and second positions 32A, 34A.

FIG. 5C shows a position 23A of the first marker of the marker arrangement 23 determined in step 106 of FIG. 3 as a weighted averaged position between the first position 32A and the second position 34A. To this end, one of the first and second positions 32A, 34A is assigned a larger weight such that the position with the larger weight contributes more to the weighted average. As a result, the determined (here: weighted averaged) position is located closer to the position with the larger assigned weight. In the example shown in FIG. 5C, the second position 34A is assigned a larger weight. As a result, the position 23A of the first marker is located closer to the second position 34A than to the first position 32A.

The weights assigned to the first and second positions 32A, 34A may be fixed, such as 60:40, 3:1, 75:25, or any other ratio. The larger weight may be assigned to the first or second marker arrangement 32, 34 (i.e., the first or second imaging modality) with the larger spatial resolution or more reliable imaging quality. For example, the second marker arrangement 34 determined from image data of the CT scanner 15 may be less dependent on a viewing angle and therefore more reliable than, for example, the first marker arrangement 32 determined from image data of the camera 16. In such a case, the second marker arrangement 34 may be assigned a larger weight than the first marker arrangement 32.

The weights assigned to the first and second positions 32A, 34A may be dependent on one ore more weight criteria. As a result, also the position 23A of the first marker may be dependent on the one or more weight criteria. FIG. 5D shows different positions 23A of the first marker of the marker arrangement 23 resulting from different weight criteria. The one or more weight criteria may be based on at least one of a viewing angle and a viewing distance. For example, first image data 28 captured at a larger viewing distance may result in a first marker arrangement 32 with a lower accuracy due to a finite spatial resolution of any imaging modality. In the example shown in FIG. 5D, the first imaging modality comprises the camera 16 and the second imaging modality comprises the CT scanner 15. As a result, the accuracy of the first position 32A may depend on the viewing angle and viewing distance of the tracker 20 relative to the camera 16. At a short viewing distance and/or optimal viewing angle (e.g., the markers 22 are at least essentially arranged in a plane perpendicular to an optical axis of the camera 16), the first image data may yield first positions 32A with a large accuracy. In such a case, the first positions 32A may be assigned a larger weight than the second positions 34A. As a result, the position 23A of the first marker depicted in FIG. 5D is arranged close to the first position 32A, such as the left-most first positions 23A. For first image data 28 captured at a larger viewing distance and/or under a less optimal viewing angle, the first position 32A may be assigned a smaller weight, resulting in the central first marker position 23A shown in FIG. 5D, or an even smaller weight, resulting in the right first marker position 23A shown in FIG. 5D. At least one of the first and second image data 28, 30 may thus comprise at least one of the viewing angle and viewing distance information for evaluation by the determining device 12.

The one or more weight criteria may additionally or alternatively be based on at least one of a temporal sequence of and a temporal offset between capturing the first image data 28 and the second image data 30. In the time between capturing the first and second image data 28, 30, the markers 22 may move relative to each other (e.g., due to movement of the patient 26 with the deformable tracker 20 as shown in FIG. 1, due to unintentional bending due to handling of the tracker 20 or due to temperature changes). In such a case, the more recently captured image data more accurately represent the actual marker arrangement 23 of interest. The first or second marker arrangement 32, 34 determined from the more recently captured image data 28, 30 may thus be assigned a larger weight. The weight assigned to the first or second positions 32A, 34A determined from the more recent image data 28, 30 may scale with the temporal offset (e.g., linearly or logarithmically).

The position 23A of a first marker 22 of the tracker 20 can be determined by combining the first position 32A and the second position 34A, such as in the ways described above. The position of the other markers 22 of the tracker 20 can be determined in the same way. As a result, the position of each marker 22 of the tracker 20 in the marker arrangement 23 can be determined. Consequently, the entire marker arrangement 23, which defines the positions of all markers 22 of the tracker 20, can be determined. As a result, the tracker arrangement 23 is calibrated based on the first and second image data.

The approach presented herein may comprise determining an invalid position of a particular marker 22 of the tracker 20 in one of the first or second arrangement 32, 34. A position of a particular marker 22 may be determined as invalid in one of the arrangements 32, 34 if a position cannot be determined at all (e.g., due to insufficient information about the particular marker 22 in the first or second image data 28, 30) or if an irregular position is identified. A position may be identified as irregular if the position is located beyond a distance threshold relative to an expected position or relative to the other markers 22 (e.g., due to movement of a patient).

Figures 6A, 6B, 6C, 6D:
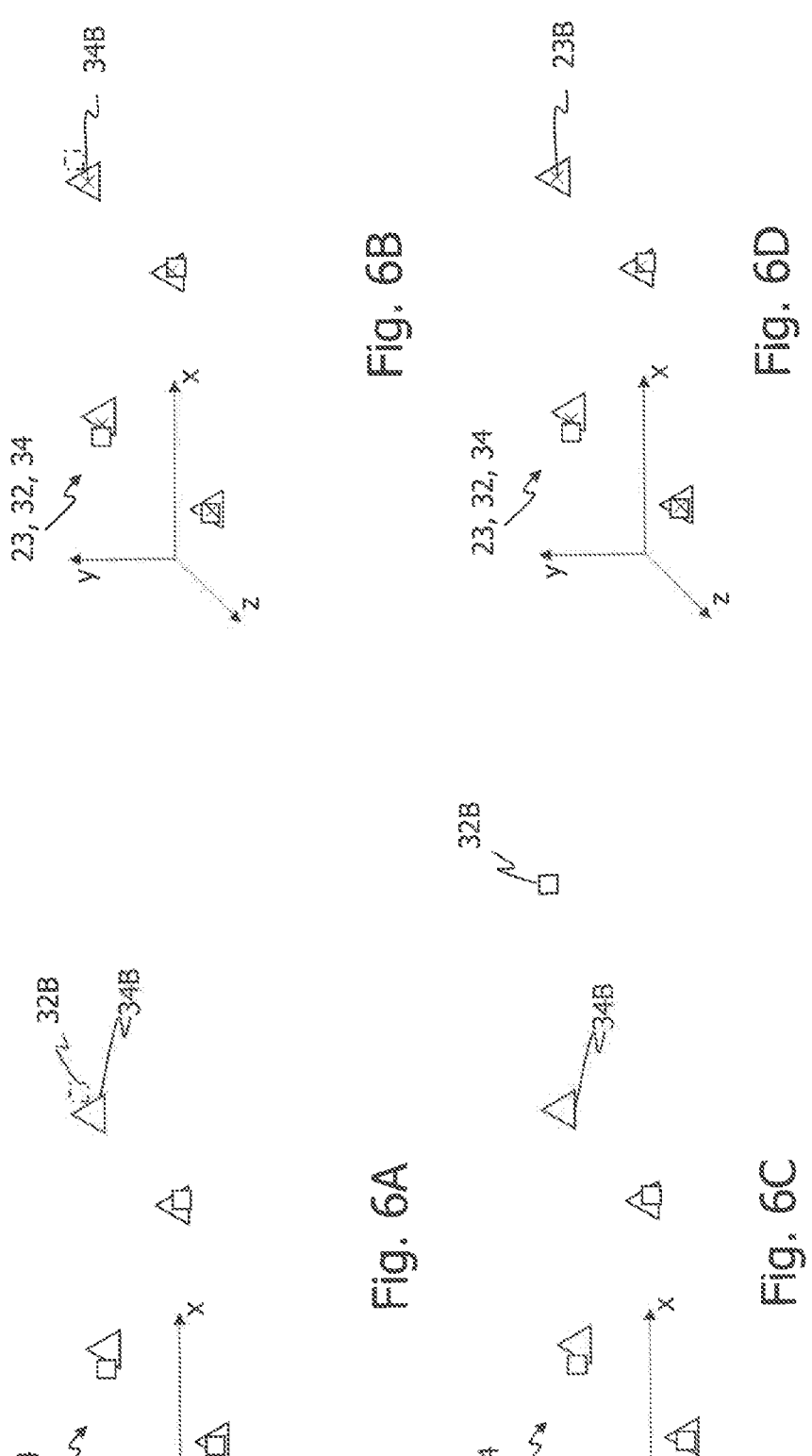
FIG. 6A shows an example of first and second marker arrangements, wherein a first position of a particular marker of the first positions is invalid.
FIG. 6B shows a marker arrangement determined based on the first and second marker arrangements shown in FIG. 6A.
FIG. 6C shows an example of first and second marker arrangements, wherein a first position of a particular marker is invalid.
FIG. 6D shows a marker arrangement determined based on the first and second marker arrangements shown in FIG. 6C.

FIG. 6A shows an example of first and second marker arrangements 32, 34, wherein a first position 32B of a particular marker 22 of the first marker arrangement 32 is invalid as it cannot be determined (e.g., because the particular marker 22 was not captured in the first image data 28 or the first image data 28 does not contain enough information for identifying the particular marker 22). The fact that the first position 32B cannot be determined is indicated in FIG. 6A by a square with dashed lines. As also illustrated in FIG. 6A, a second position 34B of the particular marker 22 can be determined in the second marker arrangement 34.

FIG. 6B shows a marker arrangement 23 (indicated by cross icons) determined in step 106 of FIG. 3 based on the first and second marker arrangements 32, 34 shown in FIG. 6A. In the example shown in FIG. 6B, the marker arrangement 23 is determined based on averaged positions (see FIGS. 5B to 5D). However, any other way for determining the marker arrangement 32 described herein may be used instead. While the positions of most markers 22 are determined as averaged positions between the first and second marker arrangements 32, 34 (as indicated by the cross icons being arranged between centres of the square and triangle icons), the position of the particular marker 22 is arranged at the centre of the second position 34B of the second marker arrangement 34. That is, instead of determining an average position of the particular marker 22, the second position 34B in the second marker arrangement 34 is selected as marker position 23B in the marker arrangement 23 due to a lack of corresponding positional information in the first arrangement 32.

FIG. 6C shows an example of first and second marker arrangements 32, 34, wherein a first position 32B of a particular marker 22 is invalid as it is located at a distance beyond a distance threshold from the other first positions in the first marker arrangement 32. Alternatively or additionally, other criteria for determining an invalid position may be used, such as distance from an expected position or distance between positions of the dedicated marker 22 of the first marker arrangement 32 and the second marker arrangement 34.

FIG. 6D shows a marker arrangement 23 determined based on the first and second marker arrangements 32, 34 shown in FIG. 6C. Similarly to the example shown in FIG. 6B, the position of the particular marker 22 is arranged at the centre of the corresponding second position 34B of the second marker arraignment 34, thus disregarding the invalid first position 32B of the first marker arrangement 32.

The approach presented herein may comprise generating an error signal when a quality criterion between positions of a marker 22 of the first arrangement 32 and the second arrangement 34 fulfils an error condition. The error condition may comprise determining an invalid position. The error signal may inform the user about the invalid position of a dedicated marker 22, which indicates that an accuracy of the determined position of the dedicated marker 22 is lower compared to the (e.g., averaged) positions of the other markers 22 in the marker arrangement 23 determined in step 106 of FIG. 3. Alternatively, or in addition, the error signal may request the user to acquire new image data or to re-position the tracker 20.

The error condition may in other cases comprise determining for a dedicated marker 22 that both, a first position of the first marker arrangement 32 and a second position of the second marker arrangement 34 are invalid. In such a case, the position of the dedicated marker 22 of the marker arrangement 23 cannot be determined.

Figure 7:
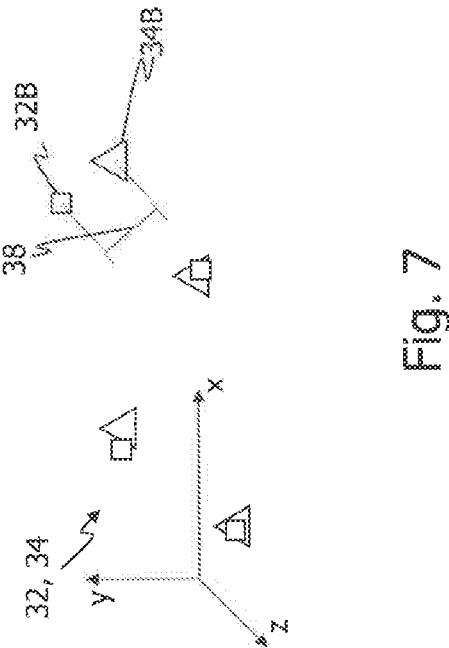
FIG. 7 shows an example of a first and second marker arrangement, wherein a position distance threshold is exceeded.

The error condition may in still other cases comprise a position distance threshold, wherein for a marker 22 a distance between a first position of the first marker arrangement 32 and a second position of the second marker arrangement 34 is to not exceed the position distance threshold. FIG. 7 shows an example of a first and second marker arrangement 32, 34, wherein the position distance threshold is exceeded. Most positions of the first and second marker arrangements 32, 34 essentially coincide, but for one of the markers 22, a first position 32B of the first marker arrangement 32 and a second position 34B of the second marker arrangement 34 are located at a comparably larger position distance 38 apart. In the example shown in FIG. 7, the position distance 38 exceeds the position distance threshold and the error signal will be generated.

It should be noted that the error condition may comprise determining an invalid position, but an error condition may be detected even when no invalid position is determined. In the example depicted in FIG. 7, the first and second positions 32B, 34B may be located close enough to an expected position and therefore both be valid positions, but when viewed in relation to each other, the first and second positions 32B, 34B are arranged at a position distance 38 that exceeds the position distance threshold. Therefore, generating the error signal can be dependent on, but also independent from determining an invalid position.

The invalid positions described above relate to image points in the image data that actually originate from markers 22 of the tracker 20. Therefore, the approach presented herein may still attempt to determine a marker position, e.g., by omitting the invalid position of one of the first and second positions and using a non-invalid position of the other one of the first and second positions instead as depicted in FIGS. 6B and 6D.

In some implementations, the first and/or second image data may include image points of non-marker surfaces that may be erroneously determined to be first or second positions. For example, the camera system 14 may captured first image data of the patient 26 with the tracker 20, wherein reflection light spots of surrounding equipment (e.g., a surgery table or surgical instruments) cause optical signals that are similar to optical signals of the markers 22. Due to the similarity, first positions may be determined from non-markers in form of the reflection light spots. As understood herein, such non-markers may also include markers of trackers different from the tracker 20.

FIG. 8A shows an example of a first arrangement 32 of markers 22 and non-markers determined from first image data captured by the camera system 14. The tracker 20 (not shown) in this example has five markers 22, but since four reflection light spots (or other non-markers) were erroneously determined as first positions, the first marker arrangement 32 comprises a total of nine first positions.

The positions of the non-markers may not (or at least to a lesser degree) be determined in the second image data, since the second image data is captured by a different imaging modality than the first image data. For example, the CT scanner 15 as second imaging modality commonly generates image data based on material density rather than optical signals (like reflections). As a result, the surfaces that cause the reflection light spots are less likely to be confused with the markers 22 in the second image data generated by the CT scanner 15. The second positions determined based on the second image data comprise less or no positions of non-markers and can therefore be used to filter out first positions of non-markers using a suitable algorithm. FIG. 8B shows an example of a second arrangement 34 determined from the second image data of the CT scanner 15. In the example shown in FIG. 8B, no second positions of a non-marker have been determined. As a result, all determined second positions are related to a marker 22 of the tracker 20.

An initial step in preparation of the actual filtering comprises matching (e.g., aligning) the first positions of the first marker arrangement 32 with the second positions of the second arrangement 34. To this end, at least one of the first and second marker arrangements 32, 34 may be rearranged (e.g., at least one of rotated, translated, and scaled) relative to the other marker arrangement 32, 34, for example until a difference between the first and second marker arrangements 32, 34 is minimized. Minimizing the difference may comprise at least one of minimizing distances between first and second positions, maximizing the number of coinciding first and second positions, and minimizing a rescaling of the first arrangement relative to the second arrangement. Matching the first and second positions may comprise using a point-set algorithm, for example an algorithm for minimizing a difference between the first and second positions, such as the Iterative Closest Point (ICP) algorithm.

FIG. 8C shows the first arrangement depicted in FIG. 8A in the resulting alignment with the second arrangement depicted in FIG. 8B. It is noted that the first and second marker arrangements 32, 34 shown in FIGS. 8A to C are arranged in a plane in order to more clearly convey the alignment. It is understood that the alignment can also be performed with three dimensional marker arrangements 32, 34.

As can be seen in FIG. 8C, five of the first positions can each be matched, or aligned, with a respective second position. However, four "spare" first positions 41 lack a respective second position to be aligned with, as the "spare" first positions 41 are the result of a misinterpretation of the first image data (and this misinterpretation did not also occur when determining the second positions).

The "spare" first positions 41 may thus be disregarded (i.e., filtered out) from the first marker arrangement 32. As a result, the risk of the first arrangement having a first position representative of a non-marker is reduced. FIG. 8D shows the first and second positions depicted in FIG. 8C, wherein "spare" first positions 41 are disregarded.

In the example shown in FIGS. 8A to D only first positions of the first marker arrangement 32 have been disregarded. Alternatively, only one or more second positions of the second arrangement 34 may be disregarded (e.g., in order to eliminate a non-marker determined from an implant captured in a CT scan). Further alternatively, one or more first and one or more second positions may be disregarded in order to eliminate non-markers from both marker arrangements 32, 34.

Any "spare" first position and "spare" second position may subsequently be disregarded in other steps described herein, such as determining the marker arrangement 23 based on the first and second marker arrangements 32, 34. Disregarding "spare" positions may comprise at least one of ignoring, removing, and zeroing a scaling factor of the spare positions.

As explained above, determining the marker arrangement 23 as shown in FIGS. 4A to 4E includes determining a first marker arrangement 32 based on the first image data 28 and a second marker arrangement 34 based on the second image data 30. An alternative approach comprises determining combined image data based on the first and second image data, wherein the marker arrangement 23 is subsequently determined based on the combined image data.

FIG. 9A shows an example of a tracker 20 with a marker arrangement 23 defining positions of markers 22, similar to the tracker 20 FIG. 4A. FIG. 9B shows first image data 28 captured of the markers 22, and FIG. 9C shows second image data 30 captured of the markers 22. FIGS. 9A to C essentially correspond to FIGS. 4A to C.

FIG. 9D shows combined image data 40 that comprises the first image data 28 and the second image data 30. Combining the first and second image data 28 may comprise identifying corresponding markers 22 in each image data 28, 30 and minimizing a sum of the distances between associated pairs of the identified markers 22. The markers 22 may be identified based on at least one of contrast, pixel intensity, a preliminary estimation of distances between markers 22, and a preliminary estimation of the marker arrangement. An image processing algorithm may be used to this end.

Alternatively or additionally, combining the first and second image data 28, 30 may be based on a known spatial relationship between first and second imaging devices (e.g., the camera system 14 and the CT scanner 15 or the MRT device) associated with the first and second imaging modality. The spatial relationship may be predetermined or acquired by tracking one of the first and second imaging devices using the other one of the first and second imaging modalities. For example, the first imaging modality may comprise the camera system 14 and the second imaging modality may comprise the CT scanner 15, wherein the CT scanner 15 comprises a tracker (e.g., attached to a frame of the CT scanner 15) that is trackable by the camera system 14.

FIG. 9E shows the marker arrangement 23 determined from the combined image data depicted in FIG. 9D. As a result, no dedicated first and second marker arrangements need to be determined in an intermediate step from the image data in the way illustrated in FIGS. 4A to 4F.

FIG. 10A shows an example of a tracker 20 that can be used with any of the techniques presented herein. The tracker 20 comprises four markers 22 (e.g., rigidly) arranged in a common plane. FIG. 10B shows a marker arrangement 23 of the tracker 20 shown in FIG. 10A as determined by any of the approaches described herein.

FIG. 10C shows a side view of the marker arrangement 23 of FIG. 10B. As can be seen (in an exaggerated way for the sake of visibility), due to a limited accuracy of the first and second image data 28, 30, the marker positions in the arrangement 23 are not precisely located in a common plane, unlike the actual markers 22 of the tracker 20 shown in FIG. 10A.

Step 106 of FIG. 3 may therefore further comprise determining a virtual plane 42 based on at least one of the first and second image data 28, 30. For example, the virtual plane 42 may be determined that fits closest to the positions of the markers 22 of the marker arrangement 23 (or any one of the first and second marker arrangements 32, 34 as illustrated in FIGS. 4D and 4E). The marker arrangement 23 as initially determined in step 106 of FIG. 3 may thus be regarded a preliminary entity that will be refined further.

Determining the virtual plane 42 may comprise determining a shortest distance relative to the positions of the marker arrangement 23 (or any one of the first and second marker arrangements 32, 34), for example by minimizing a sum of the distances or of squares of the distances between the positions relative to the virtual plane 42. Alternatively or additionally, connecting vectors between the positions and a normal vector with a minimal scalar product between the connecting vectors and the normal vector may be determined, wherein the virtual plane 42 is arranged perpendicular to the determined normal vector.

Refining the marker arrangement 23 may then further include virtually arranging the "preliminary" positions of the markers (as illustrated in FIG. 10C) in the virtual plane 42. For example, the positions may be arranged in the virtual plane 42 by projecting the positions illustrated in FIG. 10C onto the plane 42. Alternatively, the positions may be rotated onto the plane 42 around a center point located at a geometrical center of the determined positions. FIG. 10D shows the refined marker arrangement 23, wherein the positions of the marker arrangement 23 are located on the virtual plane 42.

In the example depicted in FIGS. 10A to 10D, the virtual plane 42 was determined from preliminary positions of the marker arrangement 23, whereupon the refined positions were determined by arranging the preliminary positions onto the virtual plane 42. Alternatively, the virtual plane 42 may be determined directly from at least one of the first and second image data 28, 30, not requiring determining preliminary positions of the marker arrangement 23.

Figures 11A, 11B, 11C, 11D, 11E:
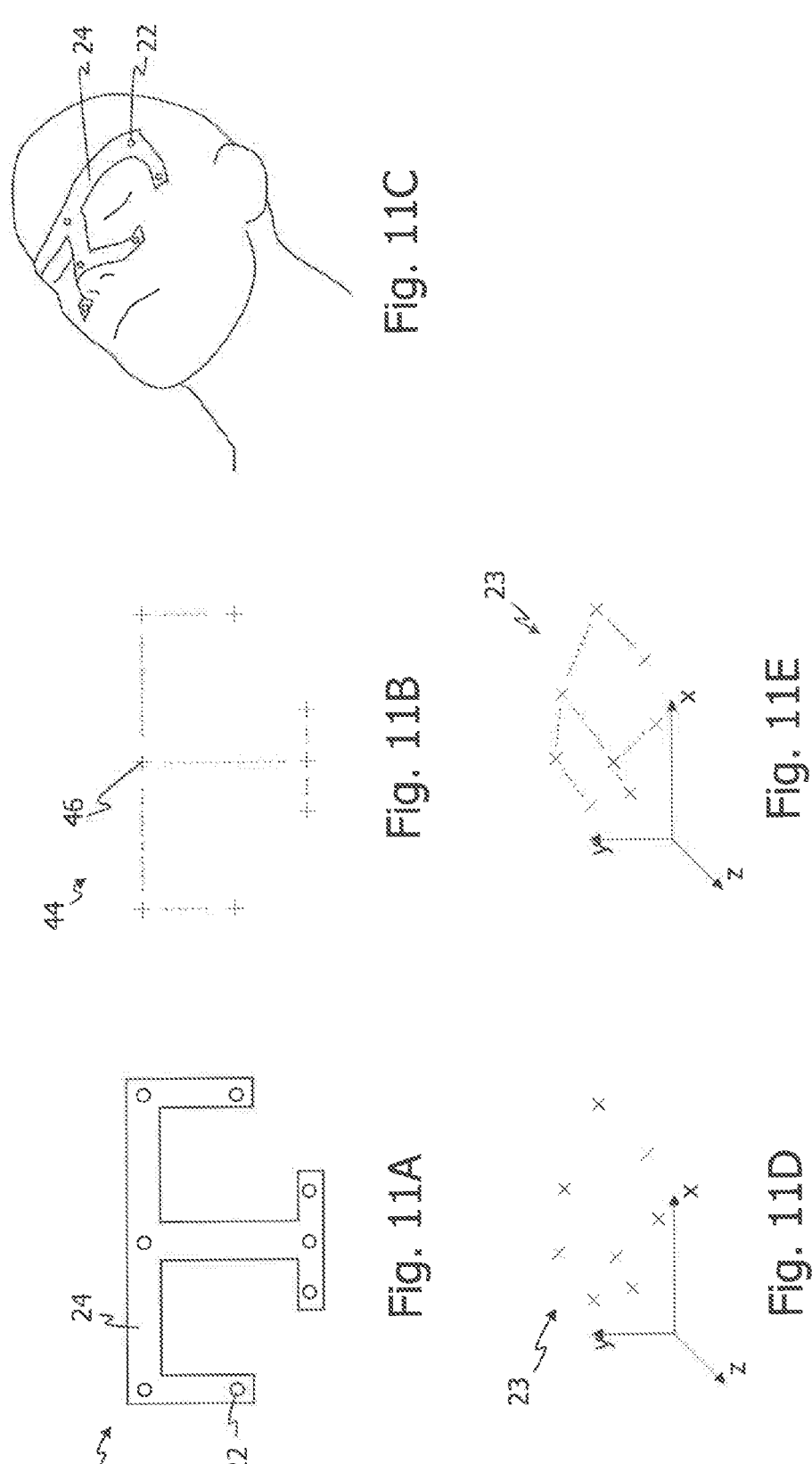
FIG. 11A shows an undeformed tracker substrate with eight markers formed thereon.
FIG. 11B shows a pre-determined marker arrangement when the substrate of FIG. 11A is undeformed.
FIG. 11C shows the substrate in a deformed shape as a result of the substrate adapting to the skin surface of a patient.
FIG. 11D shows a marker arrangement determined based on first and second image data captured of the markers supported by the deformed substrate depicted in FIG. 11C.
FIG. 11E shows a determined marker arrangement combined with a deformed pre-determined marker arrangement.

Knowledge about a pre-determined (e.g., planar) arrangement of the markers 22 of an undeformed tracker substrate 24 may also be used when determining the marker arrangement 23 in step 106 of FIG. 3. FIG. 11A shows a second example of a tracker 20 with a deformable substrate 24 supporting a plurality of markers 22, but the following observations also apply to the exemplary tracker 20 of FIG. 1 or any similar tracker. The undeformed substrate 24 may be flat, such as depicted in FIG. 11A. Alternatively, the undeformed substrate 24 may not be flat but pre-deformed, e.g., when the substrate 24 conforms to a standardized contour of a body part such as a standard face shape.

FIG. 11B shows a pre-determined marker arrangement 44 defining pre-determined positions 46 (in form of cross shaped icons) of the markers 22 when the substrate 24 is undeformed. The pre-determined marker arrangement 44 may further define pre-determined distances 48 between (e.g., pairs of) the pre-determined positions 46.

FIG. 11C shows the substrate 24 in a deformed shape as a result of the substrate 24 adapting or conforming to the skin surface of a patient, herein a region of the nose and forehead. FIG. 11D shows a preliminary marker arrangement 23 determined based on first and second image data captured of the markers 22 supported by the deformed substrate 24 depicted in FIG. 11C (see also step 106 in FIG. 3).

The preliminarily determined marker arrangement 23 may be refined based on geometrical a priori knowledge about the pre-determined marker arrangement 44, see FIG. 11B. To this end, the pre-determined marker arrangement 44 may be deformed virtually (e.g., at least one of bent, stretched, and compressed) to fit to the preliminary marker arrangement 23. To this end, the pre-determined marker arrangement 44 may be deformed in random or pre-defined pattern while aligning positions of markers of the pre-determined marker arrangement 44 with marker positions of the preliminary marker arrangement 23. The pre-determined marker arrangement 44 may be deformed while optimizing target parameters such as minimizing stretching between pre-determined positions 46 and minimizing twisting of the pre-determined marker arrangement 44. The deformed pre-determined marker arrangement can then be used to identify markers 22 of the preliminary marker arrangement 23.

FIG. 11E shows the preliminary marker arrangement 23 combined with a deformed pre-determined marker arrangement 44. The pre-determined marker arrangement 44 enables easier identification of each marker 22 and may resolve ambiguity between two closely arranged positions of markers 22. Alternatively or additionally, in the case of a bendable but non-stretchable substrate 24, the geometrical a priori knowledge about the pre-determined marker arrangement 44 may provide a maximum distance between two marker positions. The geometrical a priori knowledge may be used for determining a refined version of the preliminary marker arrangement 23 in step 106 of FIG. 3.

The method may further comprise registering at least one of the first and second image data 28, 30 with the tracker 20 using the marker arrangement 23 as determined in step 106 of FIG. 3. For example, the second image data 30 may be a CT scan that is registered with the tracker 20 using the marker arrangement 23. After registration, the tracker 20 may be tracked by the tracking system 14 using knowledge about the marker arrangement 23. Based on the resulting tracking information, the registered CT scan may be oriented on the display 18 (see FIG. 1) for navigation or other purposes. Moreover, the registered CT scan may be visualized on the display 18 in relation to a surgical instrument equipped with the tracker 20, such as a screw driver, drill or burr.

The technique for determining the marker arrangement 23 presented herein allows determining the marker arrangement 23 based on the first and second image data 28, 30 and, therefore, based on redundant sources of information. As a result, the accuracy of the determined marker arrangement 23 is improved, or calibrated. Tracking, registration and navigation are thus less prone to position or orientation errors. In other words, the accuracy of procedures that subsequently use the marker arrangement 23 is improved, such as tracking, tracker calibration and verification of the tracker type or dimensions, image registration, tracker registration, output of navigation instructions to a surgeon or surgical robot, and so on.

The features described in relation to the exemplary embodiments shown in the drawings can be readily combined to result in different embodiments. It is apparent, therefore, that the present disclosure may be varied in many ways. Such variations are not to be regarded as a departure from the scope of the invention as defined by the claims appended hereto.

The invention claimed is:

1. A method for determining a marker arrangement that defines positions of markers of a tracker, wherein the markers are detectable by a first imaging modality and a second imaging modality that is different from the first imaging modality, the method comprising:

receiving first image data of the markers that were captured using the first imaging modality;

receiving second image data of the markers that were captured using the second imaging modality; and determining the marker arrangement based on the first and second image data, wherein the marker arrangement is determined based on averaged positions of the markers between the first and second arrangements, wherein the average is weighted towards the first or second arrangement, and wherein the average is weighted based on one or more of:

(i) a temporal sequence in which the first and second image date have been taken, and (ii) at least one of a viewing angle and a viewing distance of at least one of the first and second imaging modality.

2. The method according to claim 1, wherein the marker arrangement defines at least one of (i) positions of the markers relative to each other and (ii) positions of the markers in a common coordinate system.

3. The method according to claim 1, wherein at least one of the markers has a first marker portion detectable by the first imaging modality and a second marker portion spaced apart from the first marker portion and detectable by the second imaging modality, and wherein the first marker portion is arranged in a pre-determined geometrical relationship relative to the second marker portion.

4. The method according to claim 3, wherein determining the marker arrangement is based on the pre-determined geometrical relationship.

5. The method according to claim 1, wherein at least one of the markers has a third marker portion detectable by both the first imaging modality and by the second imaging modality.

6. The method according to claim 1, wherein one of the first and second imaging modality comprises one of a computed tomography scanner and a magnetic resonance imaging scanner; and the other one of the first and second imaging modality comprises at least one camera.

7. The method according to claim 1, wherein the markers of the tracker are arranged in a common plane, and wherein determining the marker arrangement includes virtually arranging the positions of the markers in a virtual plane that is determined based on at least one of the first and second image data.

8. The method according to claim 1, further comprising registering at least one of the first and second image data, or third image data, with the tracker using the determined marker arrangement.

9. The method according to claim 1, wherein the tracker has a deformable substrate supporting the markers, wherein the markers are arranged in a pre-determined arrangement for an undeformed shape of the substrate, and wherein determining the marker arrangement for a deformed shape of the substrate is further based on the pre-determined arrangement.

10. The method according to claim 1, further comprising:

determining, based on the first image data, a first arrangement that defines first positions of the markers;

determining, based on the second image data, a second arrangement that defines second positions of the markers; and wherein the marker arrangement is determined based on a combination of the first and second arrangements.

11. The method of claim 10, further comprising:

determining an invalid position of a particular marker in at least one of the first or second arrangement; and disregarding the invalid position of the particular marker in the at least one of the first or second arrangement when determining the position of the particular marker in the marker arrangement.

12. The method of claim 10, further comprising generating an error signal when a quality criterion between positions of a marker in the first arrangement and the second arrangement fulfills an error condition.

13. The method of claim 10, further comprising:

attempting to match the first positions of the first arrangement with the second positions of the second arrangement; and disregarding at least one of (i) at least one of the first positions that lacks a matching second position and (ii) at least one of the second positions that lacks a matching first position.

14. The method according to claim 1, further comprising determining combined image data based on the first and second image data wherein the marker arrangement is determined based on the combined image data.

15. A non-transitory computer-readable storage medium comprising instructions that, when executed on at least one processor, cause the at least one processor to:

receive first image data of markers of a tracker that were captured using a first imaging modality;

receive second image data of the markers of the tracker that were captured using a second imaging modality; and determine, based on the first and second image data, a marker arrangement that defines positions of the markers of the tracker, wherein the markers are detectable by the first imaging modality and the second imaging modality that is different from the first imaging modality, wherein the marker arrangement is determined based on averaged positions of the markers between the first and second arrangements, wherein the average is weighted towards the first or second arrangement, and wherein the average is weighted based on one or more of:

(i) a temporal sequence in which the first and second image date have been taken, and (ii) at least one of a viewing angle and a viewing distance of at least one of the first and second imaging modality.

16. A system comprising:

a device for determining a marker arrangement that defines positions of markers of a tracker, wherein the markers are detectable by a first imaging modality and a second imaging modality that is different from the first imaging modality, the device being configured to:

receive first image data of the markers that were captured using the first imaging modality;

receive second image data of the markers that were captured using the second imaging modality; and determine the marker arrangement based on the first and second image data, wherein the marker arrangement is determined based on averaged positions of the markers between the first and second arrangements, wherein the average is weighted towards the first or second arrangement, and wherein the average is weighted based on one or more of:

(i) a temporal sequence in which the first and second image date have been taken, and (ii) at least one of a viewing angle and a viewing distance of at least one of the first and second imaging modality.

17. The system of claim 16, further comprising the tracker, wherein the tracker is attached to, or comprises an interface configured to be attached to, a surgical object.

\* \* \* \* \*